April 2, 1974 R. H. McCOLLEY Plant Pat. 3,535
DISTINCT VARIETY OF PHILODENDRON PLANT
Filed April 10, 1972
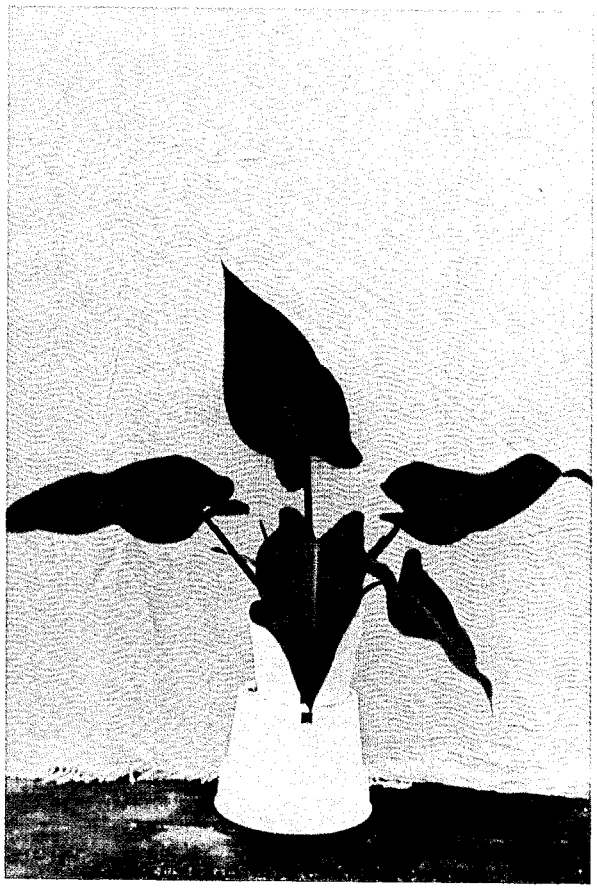

United States Patent Office

Plant Pat. 3,535

Patented Apr. 2, 1974

3,535

PHILODENDRON PLANT

Robert H. McColley, P.O. Box 17126, Orlando, Fla. 32810

Filed Apr. 10, 1972, Ser. No. 242,847
Int. Cl. A01h *5/00*
U.S. Cl. Plt.—88 1 Claim

ABSTRACT OF THE DISCLOSURE

The disclosure herein is of a Philodendron plant characterized by its resistance to wilting in low moisture and at high temperatures, its slow growth and retention of form indoors, thick, rubbery, generally long arrowhead shaped leaves which are olive grey, and the petioles and stems likewise olive grey as to the top six or seven leaves, with the bottom leaves being greyish olive green.

My present invention comprises a new and distinct variety of Philodendron plant which was developed by pollinating the standard plant in my greenhouse with pollen from a seedling selected by me from the same seedling and self breeding. More specifically my present invention is a seedling selected from a group that was the result of crossing Philodendron Burgundy with itself, using a seedling of this cross as a male parent and crossing back on to Philodendron Burgundy as a female parent. The standard plant, which is a basis for this, is from a seedling selected by me for a breeding program which has been carried on for many years, availing of the Philodendron species *wendlandii, erubescens, hastatum, imbe* and an unidentified species.

My present invention provides a color which is new to Philodendrons since it is an olive grey leaf and petiole and stem, which appear to be almost black in low light intensity conditions with excellent keeping qualities under low humidity and high temperature conditions.

My new variety has been asexually reproduced by single eye cuttings and tip cuttings in the vicinity of Orlando, Florida, and has been found to retain its distinctive characteristics through successive asexual reproduction.

My new variety has been tested under the most adverse conditions in Illinois, Ohio and Florida and has proven itself to be a superior foliage plant in each case.

My new variety is not similar to any Philodendron in cultivation, nor to any described by Graf, Bailey or Das Pflansenreich.

My new variety has certain distinctive visual features which are recognizable including the ovate leaf shape, the base of the mature leaf being auriculate and of an immature or juvenile leaf being obtuse.

The tip of such leaf is lanceolate and the veination is pinnate. The leaves have smooth midribs, with sunken veins, the surfaces being smooth to undulate.

The width of the leaves on the average is about one-half of the length. The plant form itself is vase shaped generally, the petioles being erect and of medium length.

The leaves assume horizontal to semi-erect positions and the internodes are close.

Certain general characteristics of the plant which are found particularly in my new variety include the ability to withstand extremely low light intensity and low soil moisture content for weeks.

High temperatures do not seem to bother the plant in any serious respect.

The leaves are quite thick, rubbery, and withstand brusing and dehydration as mentioned.

The plant is very resistant to bacterial soft rot and virtually immune to "shot gun" fungus.

Indoor growth is slow and the desired form is retained longer than varieties currently available.

The following detailed specifications are based on observations made in my greenhouse in Orlando, Fla. These specifications may be affected somewhat by varying environmental conditions, but where environmental conditions remain such as those present during development, including temperature, humidity and day length, the plants will reproduce and develop very uniformly.

The accompanying drawing, forming a part of the specification, shows a typical plant of my new variety, the colors being as nearly true as possible with color illustrations of this type. Color references are made to the Nickerson Color Fan published by Munsell Color Company with observations being recorded by daylight illumination under vinyl of not more than 30% shade.

(I) FORM CHARACTERISTICS

| | |
|---|---|
| (1) Leaf Shape: | |
| (a) General | Long, arrow shape. |
| (b) Mature | Lanceolate. |
| (c) Immature | Do. |
| (d) Tip | Acuminate. |
| (e) Base: | |
| (1) Mature | Auriculate. |
| (2) Immature | Obtuse. |
| (f) Displacement | Smooth to undulate. |
| (g) Margin | Entire. |
| (h) Veination | Sunken. |
| (2) Leaf attachment | Stalked. |
| (3) Leaf arrangement | Alternate, horizontal to slightly pendent. |
| (4) Petiole | Medium length; erect. |
| (5) Stem | Short heavy internodes ½" to 1". |
| (6) Overall appearance | Open—vase shape. |

(II) SIZE CHARACTERISTICS OF TYPICAL COMMERCIAL SIZE

| | Inches |
|---|---|
| (1) Leaf itself: | |
| (a) Width-widest point | 3–7 |
| (b) Width—1" from tip | ¾ |
| (c) Length | 6½–12 |
| (d) Thickness | .013–.015 |
| (2) Petiole: | |
| (a) Length | 6–10 |
| (b) Diameter (center | ¼–⅜ |
| (c) Internode spacing | ½–1 |
| (d) Stem diameter | ⅜–1 |

(III) COLOR CHARACTERISTICS

| | |
|---|---|
| (1) Leaf (top 6 or 7 leaves): | |
| (a) Top | 5Y 3/1 |
| (b) Bottom | 2.5YR 3/3 |
| (2) Leaf (old bottom leaves): | |
| (a) Top | 5GY 3/2 |
| (b) Bottom | 7.5Y 4/3 |
| (3) Leaf veination: | |
| (a) Midrib | 5Y 4/3 |
| (b) Veins | 5Y 4/3 |
| (4) Stem—darker | 2.5R 3/7 |
| (5) Petiole—darker | 2.5R 3/7 |

I claim:

1. A new and distinct variety of Philodendron plant substantially as herein disclosed, characterized as to novelty by its ability to withstand low moisture and high temperature, slow growth and form retention indoors, its thick, rubbery, generally long arrowhead shaped leaves, and olive grey leaves, petioles and stems.

No references cited.

ROBERT E. BAGWILL, Primary Examiner